United States Patent [19]

Kunz et al.

[11] Patent Number: 5,304,652
[45] Date of Patent: Apr. 19, 1994

[54] COMPOSITIONS FOR PROTECTING PLANTS FROM DISEASES

[75] Inventors: Walter Kunz, Oberwil; Rolf Schurter, Binnigen, both of Switzerland

[73] Assignee: Ciba-Geigy Corporation, Ardsley, N.Y.

[21] Appl. No.: 57,073

[22] Filed: May 4, 1993

Related U.S. Application Data

[60] Division of Ser. No. 845,518, Feb. 27, 1992, Pat. No. 5,229,384, which is a continuation of Ser. No. 586,095, Sep. 19, 1990, abandoned.

[30] Foreign Application Priority Data

Sep. 26, 1989 [CH] Switzerland .................. 3480/89
Jul. 25, 1990 [CH] Switzerland .................. 2483/90

[51] Int. Cl.$^5$ ............................................. C07D 285/14
[52] U.S. Cl. ............................................. 548/126
[58] Field of Search ..................................... 548/126

[56] References Cited

U.S. PATENT DOCUMENTS 2,494,355  1/1950  Paul ........................... 560/18
4,931,581  6/1990  Schurter ..................... 560/18

FOREIGN PATENT DOCUMENTS 384890    8/1990  European Pat. Off. .
1695786   4/1971  Fed. Rep. of Germany .
1176799   1/1970  United Kingdom .

OTHER PUBLICATIONS

P. Kirby et al., J. Chem. Soc. (C), pp. 2250-2253, (1970).

Primary Examiner—Robert Gerstl
Attorney, Agent, or Firm—Roberts Edward McC.; Kevin T. Mansfield

[57] ABSTRACT

Novel benzo-1,2,3-thiadiazole derivatives of the formula

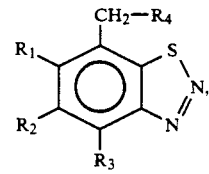

in which $R_4$ is Hal or OH; $R_1$, $R_2$ and $R_3$ independently of one another are hydrogen, halogen, methyl, methoxy or methylthio.

2 Claims, No Drawings

COMPOSITIONS FOR PROTECTING PLANTS FROM DISEASES

This is a divisional of Ser. No. 07/845,518, filed Feb. 27, 1992, now U.S. Pat. No. 5,229,384 which is a continuation of Serial No. 07/586,095, filed Sep. 19, 1990, now abandoned.

The present invention relates to novel benzo-1,2,3-thiadiazole derivatives of the following formula I. The invention furthermore relates to the preparation of these substances and the compositions containing at least one of these compounds as active substances. The invention moreover relates to the preparation of the compositions mentioned and the use of the active substances or the compositions for protecting plants from attack by harmful microorganisms, for example phytopathogenic fungi, bacteria and viruses.

The compounds according to the invention are those of the general formula I

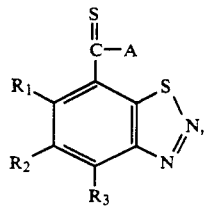
(I)

in which $R_1$, $R_2$ and $R_3$ independently of one another are hydrogen, halogen, methyl, methoxy or methylthio; A is $-OR_4$, $-SR_4$, $-N(R_5)R_6$, $-N(R_7)-N(R_5)R_6$, $-O-N=C(R_8)R_9$, $-N(R_7)-OR_{10}$, or

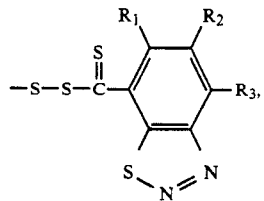

$R_4$ is hydrogen or one molar equivalent of a metal ion or of a protonated organic base, $C_1-C_{18}$alkyl, $C_3-C_{35}$alkyl which is interrupted by an oxygen or sulfur atom, $C_1-C_8$alkyl which is substituted by halogen or $-COOR_7$, $C_3-C_6$alkenyl which is unsubstituted or substituted by halogen, $C_3-C_6$alkinyl which is unsubstituted or substituted by halogen, $C_4-C_7$cycloalkyl which is unsubstituted or substituted by halogen or methyl, an aryl or heterocyclic radical U having not more than 3 heteroatoms O, N and/or S, or a radical U which is linked via an alkylene bridge containing not more than 6 carbon atoms and up to 2 oxygen atoms; U is phenyl, phenoxyphenyl, biphenyl or 1- or 2-naphthyl, each of which is unsubstituted or substituted by halogen, $C_1-C_3$alkyl or $C_1-C_4$alkoxy, or a saturated or unsaturated 5- to 7-membered heterocyclic radical T which is unsubstituted or substituted by one or more substituents from the group comprising halogen, $C_1-C_3$alkyl and/or $C_1-C_3$alkoxy; $R_5$ and $R_6$ independently of one another are hydrogen, $C_1-C_8$alkyl, $C_1-C_6$alkyl which is substituted by $C_1-C_3$alkoxy and/or cyano, or $C_3-C_6$alkenyl, $C_3-C_6$alkinyl, $C_3-C_7$cycloalkyl, a radical U or a radical U which is linked via an alkylene bridge containing not more than 2 C atoms; or $R_5$ and $R_6$, together with the nitrogen atom, are a 5- to 7-membered heterocyclic radial W which is unsubstituted or substituted by methyl and has not more than 2 further heteroatoms O, N and/or S; $R_7$ is hydrogen or $C_1-C_4$alkyl; $R_8$ and $R_9$ independently of one another are hydrogen, $C_1-C_6$alkyl, cyano, $CONH_2$, $CONHCONHR_7$, or phenyl which is unsubstituted or substituted by halogen, $C_1-C_3$alkyl or $C_1-C_3$alkoxy; or, together with the connecting carbon atom, are also a 5- to 7-membered carbocyclic radical; and $R_{10}$ is hydrogen, $C_1-C_6$alkyl, $C_3-C_6$alkenyl, $C_5-C_7$cycloalkyl, phenyl or benzyl.

Cycloalkyl radicals and carbocyclic rings are, for example, cylopropane, cyclobutane, cyclopentane, cyclohexane or cycloheptane, preferably cylopropane, cyclopentane and cyclohexane. A heterocyclic radical T is to be understood as meaning, for example, pyrrolidin-1-yl, piperidin-1-yl, azocyclohept-1-yl, morpholin-4-yl, 2,6-dimethylmorpholin-4-yl, imidazol-1-yl, 1,2,4-triazol-1-yl, pyrrol-1-yl, 2-, 3- or 4-pyridyl, 2-, 4- or 5-pyrimidyl, isoxazolyl-3- or 5-yl, 2-thienyl, 2-furanyl, 2-thiazolyl, 1,3,4-thiadiazol-2-yl, tetrahydrofuran-2-on-3-yl or tetrahydropyran-2-on-3-yl, or tetramethylpiperidin-4-yl.

Heterocyclic radicals W are pyrrolidine, piperidine, azocycloheptane, morpholine, 2,6-dimethylmorpholine, imidazol-1-yl, 1,2,4-triazol-1-yl or pyrrol-1-yl.

Halogen is fluorine, chlorine, bromine or iodine, preferably fluorine, and further in the sequence chlorine, bromine and iodine. 1 to 3 halogen atoms can appear as substituents in individual radicals.

Alkyl itself or as a constituent of another substituent is to be understood as meaning straight-chain or branched alkyl radicals. Depending on the stated number of carbon atoms, these are, for example, the following preferred groups: methyl, ethyl and the isomers of propyl, butyl, pentyl or hexyl, for example isopropyl, isobutyl, tert-butyl, sec-butyl or isopentyl.

Alkenyl is, for example, 1-propenyl, allyl, 1-butenyl, 2-butenyl or 3-butenyl, and alkinyl is, for example, 2-propinyl, 1-butinyl or 4-pentinyl.

Salt-forming amines are, for example: trimethylamine, triethylamine, tripropylamine, tributylamine, tribenzylamine, tricyclohexylamine, triamylamine, trihexylamine, N,N-dimethylaniline, N,N-dimethyltoluidine, N,N-dimethyl-p-amino-pyridine, N-methyl-pyrrolidine, N-methylpiperidine, N-methyl-pyrrolidine, N-methylimidazole, N-methyl-pyrrole, N-methylmorpholine, N-methylhexamethyleneimine, pyridine, quinoline, alpha-picoline, β-picoline, isoquinoline, pyrimidine, acridine, N,N,N', N'-tetramethylethylenediamine, N,N,N',N'-tetraethylethylenediamine, quinoxaline, N-propyldiisopropylamine, N,N-dimethylcyclohexylamine, 2,6-lutidine, 2,4-lutidine, triethylenediamine and heterocyclic amines of the morpholine type.

The bases or compounds of basic character are inorganic bases or agents which form bases, for example hydroxides, carbonates and bicarbonates of the alkali metals and alkaline earth metals, preferably LiOH, NaOH, KOH, $Mg(OH)_2$ or $Ca(OH)_2$; and furthermore $NaHCO_3$, $KHCO_3$, $Na_2CO_3$ and $K_2CO_3$.

The compounds of the formula I can be classified into the following groups on the basis of their particular plant protection properties:

1. Compounds of the formula I in which: $R_1$, $R_2$ and $R_3$ independently of one another are hydrogen, fluorine or methyl; A is $-OR_4$, $-SR_4$, $-N(R_5)R_6$, $-N(R_7)-N(R_5)R_6$, $-O-N=C(R_8)R_9$, $-N(R_7)-OR_{10}$ or

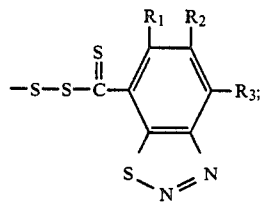

$R_4$ is hydrogen, one molar equivalent of a metal ion or of a protonated organic base, $C_1$-$C_6$alkyl, $C_5$-$C_6$cycloalkyl, phenyl, benzyl, tetrahydrofuran-2-on-3-yl, 2-, 3- or 4-pyridyl, 2-, 4- or 5-pyrimidyl or (2,2-dimethyldioxolan-4-yl)-methyl; $R_5$ and $R_6$ independently of one another are hydrogen, $C_1$-$C_4$alkyl, $C_1$-$C_3$alkyl which is substituted by methoxy, ethoxy and/or cyano, or allyl, propargyl, $C_3$-$C_6$cycloalkyl, phenyl, benzyl, phenethyl, 2-furfurylmethyl, tetrahydrofuran-2-on-3-yl, 2,3- or 4-pyridyl, 2-, 4- or 5-pyrimidyl, $R_7$ is hydrogen, methyl or ethyl; or the group $N(R_5)R_6$ together forms a pyrrole, pyrrolidine, imidazol-1-yl, 1,2,4-triazol-1-yl, piperidine, morpholine or 2,6-dimethylmorpholine ring; $R_8$ and $R_9$ independently of one another are hydrogen, $C_1$-$C_6$alkyl, cyano, the radicals $CONH_2$, $CONH$-$CONHR_7$ or phenyl, or, together with the connecting carbon atom, form a 5- to 7-membered carbocyclic radical; and $R_{10}$ is hydrogen, $C_1$-$C_3$alkyl, allyl, $C_5$-$C_6$cycloalkyl, phenyl or benzyl.

2. Compounds of the formula I, in which: $R_1$, $R_2$ and $R_3$ independently of one another are hydrogen, fluorine or methyl; A is $-OR_4$, $-SR_4$, $-N(R_5)R_6$, $-N(R_7)-N(R_5)R_6$, $-O-N=C(R_8)R_9$ or $-N(R_7)-OR_{10}$; $R_4$ is hydrogen or one molar equivalent of a metal ion or of a tertiary amine, $C_1$-$C_6$alkyl, $C_5$-$C_6$cycloalkyl, phenyl, benzyl, tetrahydrofuran-2-on-3-yl or 2-, 3- or 4-pyridyl; $R_5$ and $R_6$ independently of one another are hydrogen, $C_1$-$C_3$alkyl, $C_1$-$C_3$alkyl which is substituted by methoxy and/or cyano, or allyl, propargyl, $C_3$-$C_5$cycloalkyl, phenyl, benzyl, 2-furfuryl, tetrahydrofuran-2-on-3-yl, 2-, 3- or 4-pyridyl, 2-, 4- or 5-pyrimidyl or piperidin-1-yl, or the group $N(R_5)R_6$ together is a pyrrolidine, imidazol-1-yl, piperidine, morpholine or 2,6-dimethylmorpholine ring; $R_7$ is hydrogen, methyl or ethyl; $R_8$ and $R_9$ independently of one another are hydrogen, methyl, ethyl or the radicals cyano, $CONH_2$, phenyl or benzyl, or, together with the connecting carbon atom, are cyclopentyl or cyclohexyl; and $R_{10}$ is hydrogen, methyl, ethyl, allyl, $C_3$-$C_5$cycloalkyl or phenyl.

3. Compounds of the formula I in which: $R_1$, $R_2$ and $R_3$ independently of one another are hydrogen or fluorine; A is $-OR_4$, $-SR_4$, $-N(R_5)R_6$ or $-N(R_7)-N(R_5)R_6$; $R_4$ is hydrogen, Li+, Na+, K+, ½ Mg$^{2+}$, ½ Ca$^{2+}$, +HN($C_1$-$C_4$alkyl)$_3$, $C_1$-$C_4$alkyl, $C_5$-$C_6$cycloalkyl, phenyl, benzyl, 2-, 3- or 4-pyridyl or 2-, 4- or 5-pyrimidyl; $R_5$ and $R_6$ independently of one another are hydrogen, methyl, ethyl, allyl, propargyl, phenyl, benzyl, 2-furanylmethyl or 2-, 3- or 4-pyridyl, or the group $N(R_5)R_6$ together is a pyrrolidine, piperidine, morpholine, 2,6-dimethylmorpholine or imidazol-1-yl ring; and $R_7$ is hydrogen, methyl or ethyl.

The following compounds are distinguished by particularly advantageous plant protection properties:

O-ethyl benzo-1,2,3-thiadiazole-7-thiocarboxylate (compound 1.2);

S-methyl benzo-1,2,3-thiadiazole-7-thiocarboxylate (compound 1.6);

benzo-1,2,3-thiadiazole-7-carboxylic acid thioamide (compound 2.1);

7-[benzo-1,2,3-thiadiazole]-N',N'-dimethylthiohydrazide (compound 3.1);

S-ethyl benzo-1,2,3-thiadiazole-7-thiocarboxylate (compound 1.7);

S-propyl benzo-1,2,3-thiadiazole-7-thiocarboxylate (compound 1.8);

S-cyclopentyl benzo-1,2,3-thiadiazole-7-thiocarboxylate (compound 1.15);

benzo-1,2,3-thiadiazole-7-thiocarboxylic acid morpholide (compound 2.15); and benzo-1,2,3-thiadiazole-7-thiocarboxylic acid piperidide (compound 2.43).

It has now been found, surprisingly, that the compounds of the formula I according to the invention prevent the attack of plants by harmful microorganisms when they are used, and thus prevent damage to the plants caused by the attack. It is characteristic of the active substances according to the invention that the protection of the plants can occur either by direct action on the phytopathogenic microorganisms by means of leaf application or soil application or by activation and stimulation of the defence system endogenous to the plant (immunisation). The great advantage of the compounds of the formula I is that it can be ensured that the plants treated with these substances preserve their health under their own power without using further microbicidal substances during the vegetation period. By using the active substances according to the invention, it is consequently possible to avoid adverse side effects such as may appear during direct parasite control using chemical substances, for example on the hand by damage to the crop plants (phytotoxicity) and on the other hand by causing resistance phenomena in the harmful microorganisms, this advantageously resulting in a completely undisturbed growth of the crop plants.

On the basis of the double mode of action of the compounds of the formula I according to the invention, that is to say on the one hand the direct control of phytopathogens and on the other hand the increase in the general power of resistance of the plants treated with these active substances due to immunisation, wide-ranging protection of the plants against diseases can be achieved. The use of the active substances according to the invention is therefore particularly suitable for conditions in practice. The intrinsic systemic activity of the compounds of the formula I moreover means that the protective effect also extends to additionally growing parts of plants on the treated plants.

The general plant protection activity of the active substances according to the invention is effective, for example, against the phytopathogenic fungi belonging to the following classes: Fungi imperfecti (for example Botrytis, Helminthosporium, Fusarium, Septoria, Cercospora and Alternaria); Basidiomycetes (for example Hemileia, Rhizocotonia and Puccinia); and Ascomycetes (for example Venturia, Podosphaera, Erysiphe, Monilinia and Uncinula).

The active substances can moreover be particularly advantageously employed against the following harmful organisms: fungi, for example Oomycetes (for example *Plasmopara viticola, Phytophthora infestans, Peronospora tabacina, Pseudoperonospora* and *Bremia letucae*), Fungi imperfecti (for example *Colletotrichum*

*lagenarium*, *Piricularia oryzae* and *Cercospora nicotinae*), Ascomycetes (for example *Venturia inaequalis*); bacteria, for example Pseudomonads (for example *Pseudomonas lachrymans*, *Pseudomonas tomato* and *Pseudomonas tabaci*); Xanthomonads (for example *Xanthomonas oryzae* and *Xanthomonas vesicatoria*); Erwinia (for example *Erwinia amylovora*); and viruses, for example tobacco mosaic virus.

The compounds according to the invention can be used for protecting plants in various useful crops.

The following species of plants are suitable, for example, for use of the compounds of the formula I according to the invention in the context of the invention: cereals (wheat, barley, rye, oats, rice, sorghum and related species); beet (sugar beet and feed beet); pomaceous, stone and soft fruit (apples, pears, plums, peaches, almonds, cherries, strawberries, raspberries and blackberries); pulses (beans, lentils, peas, and soya); oil crops (rape, mustard, poppy, olive, sunflower, coconut, castor, cacao and peanut); cucumber plants (pumpkins, cucumbers, melons); fibre plants (cotton, flax, hemp and jute); citrus fruits (oranges, lemons, grapefruits and mandarins); vegetable varieties (spinach, lettuce, asparagus, cabbage varieties, carrots, onions, tomatoes, potatoes and paprika); bay-leaf plants (avacado, cinnamon and camphor) or plants such as maize, tobacco, nuts, coffee, cane sugar, tea, wine vines, hops, banana and natural rubber plants and ornamental plants (flowers, shrubs, hardwood trees and softwood trees, such as conifers). This list does not represent a limitation.

The following plants are particularly suitable target crops for use of the process according to the invention: cucumber, tobacco, vines, rice, pepper, potatoes, tomatoes, wheat, barley, pears and apples.

The present invention moreover relates to compounds of the formulae III, V and VI

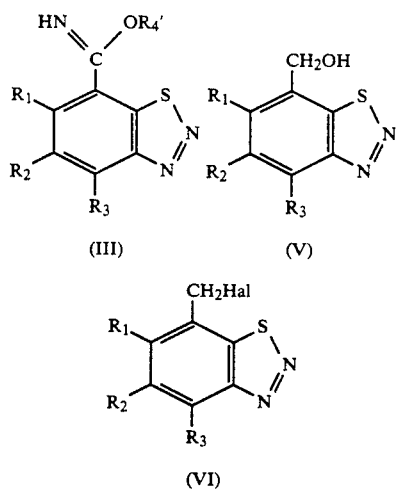

in which: $R_1$, $R_2$ and $R_3$ independently of one another are hydrogen, halogen, methyl, methoxy or methylthio; $R_4'$ is $C_1$-$C_{18}$alkyl, $C_3$-$C_{35}$alkyl which is interrupted by an oxygen or sulfur atom, $C_1$-$C_8$alkyl which is substituted by halogen or —$COOR_7$; $C_3$-$C_6$alkenyl which is unsubstituted or substituted by halogen, $C_3$-$C_6$alkinyl which is unsubstituted or substituted by halogen, $C_4$-$C_7$cycloalkyl which is unsubstituted or substituted by halogen or methyl, an aryl or heterocyclic radical U which is having not more than 3 heteroatoms O, N and/or S, or a radical U which is linked via an alkylene bridge containing not more than 6 carbon atoms and up to 2 oxygen atoms; U is phenyl, phenoxyphenyl, biphenyl or 1- or 2-naphthyl, each of which is unsubstituted or substituted by halogen, $C_1$-$C_3$alkyl or $C_1$-$C_4$alkoxy, or a saturated or unsaturated 5- to 7-membered heterocyclic radical T which is unsubstituted or substituted by one or more substituents from the group comprising halogen, $C_1$-$C_3$alkyl and/or $C_1$-$C_3$alkoxy; and Hal is halogen, preferably chlorine. These compounds are novel. On the one hand they function according to the invention as intermediates in the synthesis of the compounds of the formula I, and on the other hand they form independent groups of fungicidally active compounds. Like the compounds of the formula I, they can be used as active substances against phytopathogenic microorganisms, in particular against fungi, for protection of the abovementioned plant crops.

The following compounds are preferred active substances having particularly advantageous plant protection properties:

7-hydroxymethyl-benzo-1,2,3-thiadiazole (compound no. 6.1);

7-chloromethyl-benzo-1,2,3-thiadiazole (compound no. 7.1); and benzo-1,2,3-thiadiazole-7-ethyl ester-imide hydrochloride (compound no. 5.2).

The compounds of the formula I are prepared in groups as follows:

A) reaction of a compound of the formula IIa

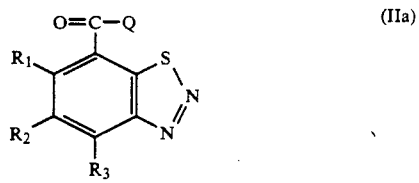

with a thionating reagent, for example with phosphorus pentasulfide ($P_4S_{10}$) or Lawesson's reagent [2,4-bis(4-methoxyphenyl)-1,3,2,4-dithiadiphosphetane 2,4-disulfide] in an aprotic non-polar or slightly polar solvent at temperatures of 20° to 200° C., preferably 60° to 150° C., Q being the radicals —$OR_4$, —$SR_4$ or —$N(R_5)R_6$, to give a compound of the formula Ia

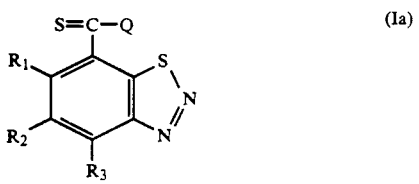

wherein $R_1$, $R_2$ and $R_3$ are as defined under formula I;

$B_1$) reaction of the solution of a nitrile of the formula II

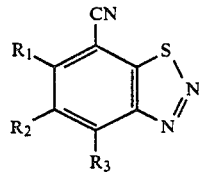
(II)

in an alcohol of the formula R₄'OH, in which R₄' is as defined under formula III, by passing gaseous hydrogen halide, preferably hydrogen chloride, in at temperatures of −20° to 80° C., preferably −10° to 40° C., to give an imidate of the formula III

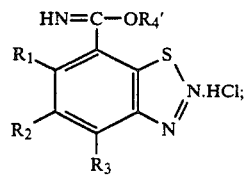
(III)

and

B₂) subsequent reaction of the resulting compound of the formula III with hydrogen sulfide in non-polar or weakly polar solvents in the presence of a base at temperatures of −20° to 80° C., preferably −5° to 40° C., to give the thiocarboxylic acid esters of the formula Ia'

(Ia')

in which R₁, R₂ and R₃ are as defined under formula I and R₄' is as defined under formula III;

C) reaction of a thiono compound of the formula IV

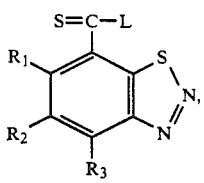
(IV)

in which L has the meaning of chlorine, or of an azolide of the formula

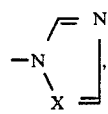

in which X is CH or N or has the meaning of —S—C-₁-C₄alkyl, —S—CH₂COOM or SM, in which M is hydrogen or an alkali metal ion;

(C₁) with an alcohol or a thiol of the formula R₄'OH or R₄'SH, in which R₄' is as defined for R₄, with the exception of hydrogen, a protonated organic base or a metal atom, to give a compound of the formula Ia' or Ia''

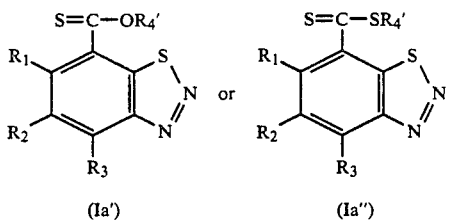

(Ia')    (Ia'')

or (C₂) with an oxime of the formula HON=C(R₇)R₈ to give a compound of the formula Ib $$S=C-O-N=C\begin{array}{c}R_7\\R_8\end{array}$$ (Ib)

[benzothiadiazole ring with R₁, R₂, R₃ substituents]

or (C₃) with an amine of the formula HN(R₅)R₆, to give a compound of the formula Ic $$S=C-O-N(R_5)R_6$$ (Ic)

[benzothiadiazole ring with R₁, R₂, R₃ substituents]

or (C₄) with a hydroxylamine derivative of the formula HN(R₇)—O—R₁₀, to give a compound of the formula Id $$S=C-N(R_7)-O-R_{10}$$ (Id)

[benzothiadiazole ring with R₁, R₂, R₃ substituents]

or (C₅) with a hydrazine derivative of the formula HN(R₇)—N(R₅)R₆, to give a compound of the formula Ie $$S=C-N(R_7)-N(R_5)R_6$$ (Ie)

[benzothiadiazole ring with R₁, R₂, R₃ substituents]

in inert solvents with or without a base at a temperature of −20° to 170° C.;

D) alkylation of the dithio acid or its salt of the formula IVa

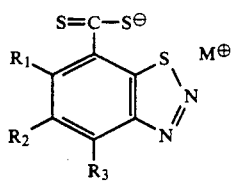

($M^\oplus$ = hydrogen or an alkali metal ion) with an alkylating agent of the formula $R_4'$-L, in which $R_4'$ is as defined for $R_4$, with the exception of hydrogen, a metal ion or a protonated organic base and L is a leaving group, in the presence of a base in inert solvents at temperatures of $-30°$ to $110°$ C. to give a compound of the formula Ia''

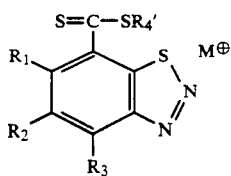

E) oxidation of the dithio acid or its salt of the formula IVa with atmospheric oxygen, potassium hexacyanoferrate(III) or $KI/I_2$ in aqueous solution at temperatures of $10°$ to $60°$ C. to give a compound of the formula If

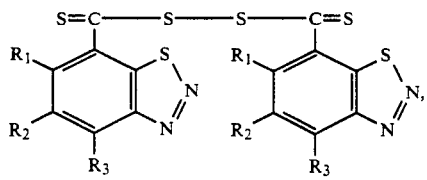

in which in the above formulae $R_1$ to $R_{10}$ are as defined under formula I.

Organic and inorganic bases for the preparation processes described above, where necessary, are, for example, tertiary amines, such as trialkylamines (trimethylamine, triethylamine, tripropylamine and the like), pyridine bases (pyridine, 4-dimethylaminopyridine, 4-pyrrolidylaminopyridine or collidine), oxides and hydroxides, carbonates and bicarbonates of alkali metals and alkaline earth metals and alkali metal acetates.

Suitable solvents and diluents which are inert in the reaction are used as reaction media according to the particular reaction conditions. Examples are: aliphatic and aromatic hydrocarbons, such as benzene, toluene, xylenes and petroleum ether; halogenated hydrocarbons, such as chlorobenzene, methylene chloride, ethylene chloride, chloroform, carbon tetrachloride and tetrachloroethylene; ethers and ether-like compounds, such as dialkyl ethers (diethyl ether, diisopropyl ether, tert-butylmethyl ether and the like), anisole, dioxane and tetrahydrofuran; nitriles, such as acetonitrile and propionitrile; N,N-dialkylated amides, such as dimethylformamide; ketones, such as acetone, diethyl ketone and methyl ethyl ketone; and mixtures of such solvents with one another.

The processes for the preparation of the compounds of the formula I are methods which are known to the expert or described in the literature (compare Tetrahedron 41, 5061 (1985); Thio- and dithiocarboxylic Acids and their Derivatives in A. Senning, Topics in Sulfur Chemistry Volume 4, 1979; and Houben-Weyl E5, Part 2, pages 790, 796, 906–909, 921, 930/931).

The compounds of the formula IV which function as intermediates for the compounds of the formula I can be prepared as follows by known methods:

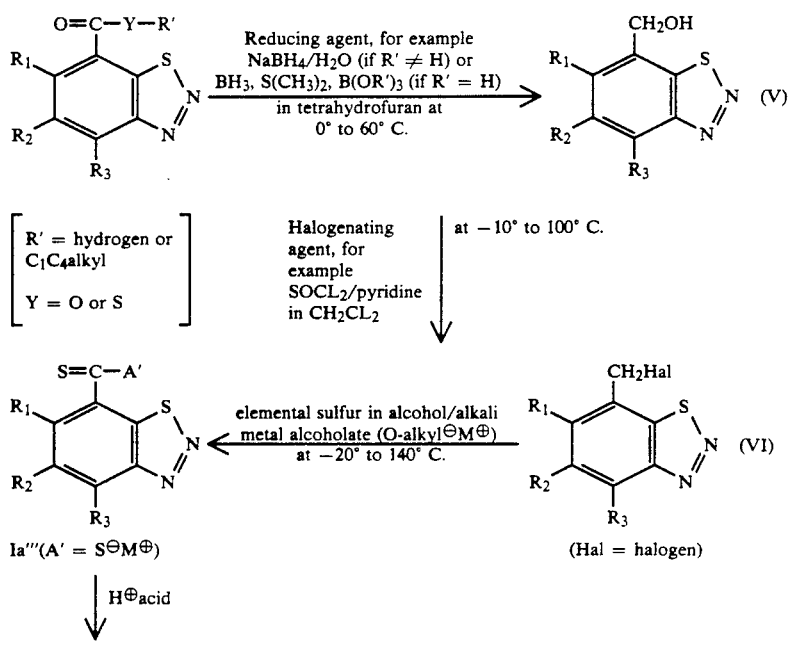

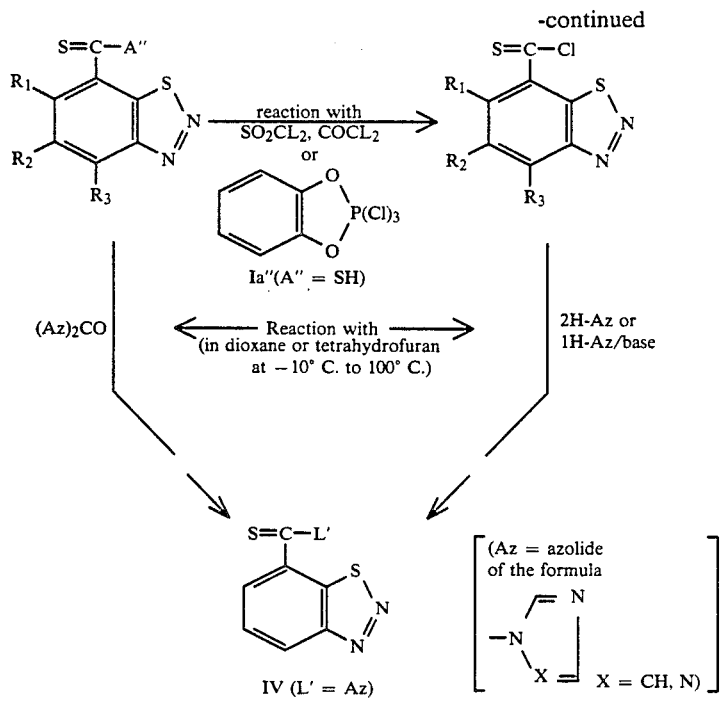

The preparation processes described above are methods which are known to the expert or described in the literature (compare Chem. Ber. 98, 829 (1965); Helv. Chim. Acta 3, 824 (1920); German Offenlegungsschrift 2,306,543, Ann. Chem. 739, 201 (1970); Houben-Weyl E5, 914 and European patent 313,512.

The invention relates to the microbicidal compositions for protecting plants from diseases which are used in the context of the invention and contain the compounds of the formula I as active substances.

Active substances of the formula I are usually used in the form of compositions and can be applied to the plants or their environment simultaneously with or in succession with other active substances. These other active substances can be either fertilizers, agents which donate trace elements or other preparations which influence plant growth. However, they can also be selective herbicides, insecticides, fungicides, bactericides, nematicides, molluscicides or mixtures of several of these preparations, if appropriate together with other carrier substances conventionally used in the art of formulation, surfactants or other additives which promote application.

Suitable carriers and additives can be solid or liquid and correspond to the substances appropriate in the art of formulation, for example naturally occurring or regenerated mineral substances, solvents, dispersants, wetting agents, tackifiers, thickeners, binders or fertilizers.

One process for using an active substance of the formula I or an agrochemical composition containing at least one of these active substances is application to the plants (leaf application). However, the active substances of the formula I can also enter the plant through the root system via the soil (soil application) by impregnating the location of the plants with a liquid preparation or incorporating the substances into the soil in solid form, for example in the form of granules. However, the compounds of the formula I can also be applied to seeds (coating) either by soaking the seeds in a liquid preparation of the active substance or coating them with a solid preparation (dressing application). Other types of application are moreover possible in particular cases, thus, for example, controlled treatment of the plant stem or of the bud.

The compounds of the formula I are employed here in unchanged form or preferably together with the auxiliaries conventionally used in the art of formulation. For this purpose they are processed in a known manner to, for example, emulsion concentrates, brushable pastes, directly sprayable or dilutable solutions, dilute emulsions, wettable powders, soluble powders, dusts or granules, by encapsulation, for example in polymeric substances. The use processes, such as spraying, misting, dusting, sprinkling, brushing or watering, like the nature of the compositions, are chosen according to the aims sought and the given circumstances. Favourable application amounts are in general 50 g to 5 g of active substance (AS) per ha; preferably 100 g to 2 kg AS/ha, in particular 100 g to 600 g of AS/ha.

The formulations, that is to say the compositions, preparations or combinations containing the active substance of the formula I and if appropriate a solid or liquid additive, are prepared by intimately mixing and/or grinding the active substances with extenders, for example with solvents, solid carriers and if appropriate surface-active compounds (surfactants).

Possible solvents are: aromatic hydrocarbons, preferably $C_8$ to $C_{12}$ fractions, for example xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol or ethylene glycol monomethyl or -ethyl ether, ketones, such as cyclohexanone, strongly polar solvents, such as N-methyl-2-pyrrolidone, dimethylsulfoxide or dimethylformamide; and if appropriate epoxidized vegetable oils, such as epoxidized coconut oil or soya oil, or water.

The solid carriers used, for example for dusts and dispersible powders, are as a rule naturally occurring ground minerals, such as calcite, talc, kaolin, montmorrilonite or attapulgite. Highly disperse silicic acid or highly disperse absorbent polymers can also be added to improve the physical properties. Granular adsorptive granule carriers are porous types, for example pummice, broken brick, sepiolite or bentonite, and non-adsorptive carrier materials are, for example, calcite or sand. A large number of pregranulated materials of inorganic or organic nature, such as, in particular, dolomite or comminuted plant residues, can moreover be used.

Surface-active compounds are, depending on the nature of the active substance of the formula I to be formulated, nonionic, cationic and/or anionic surfactants having good emulsifying, dispersing and wetting properties. Surfactants are also to be understood as meaning surfactant mixtures.

The cationic surfactants are in particular quaternary ammonium salts which contain at least one alkyl radical having 8 to 22 C atoms as N substituents and lower, free or halogenated alkyl, benzyl or lower hydroxyalkyl radicals as further substituents.

Suitable anionic surfactants can be either so-called water-soluble soaps or water-soluble synthetic surface-active compounds.

Soaps are the alkali metal, alkaline earth metal or unsubstituted or substituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil.

Synthetic surfactants which can be used are, in particular, fatty alcohol sulfonates, fatty alcohol sulfates, sulfonated benzimidazole derivatives or alkylsulfonates. The fatty alcohol sulfonates or sulfates are as a rule in the form of alkali metal, alkaline earth metal or unsubstituted or substituted ammonium salts and contain an alkyl radical having 8 to 22 C atoms.

Non-ionic surfactants are in particular polyglycol ether derivatives of aliphatic or cycloaliphatic alcohols, saturated or unsaturated fatty acids and alkylphenols, which can contain 3 to 30 gycol ether groups and 8 to 20 carbon atoms in the (aliphatic) hydrocarbon radical and 6 to 18 carbon atoms in the alkyl radical of the alkylphenols.

The agents can also contain other additives, such as stabilizers, foam suppressants, viscosity regulators, binders, tackifiers and fertilizers, or other active substances to achieve specific effects.

The agrochemical preparations as a rule contain 0.1 to 99% by weight, in particular 0.1 to 95% by weight, of active substance of the formula I, 99.9 to 1% by weight, in particular 99.8 to 5% by weight, of a solid or liquid additive and 0 to 25% by weight, in particular 0.1 to 25% by weight, of a surfactant.

The following examples serve to further illustrate the invention, without limiting it.

1. PREPARATION EXAMPLES

1.1 Preparation of O-ethyl benzo-1,2,3-thiadiazole-7-thiocarboxylate (compound 1.2)

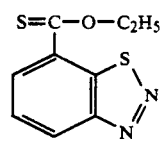

A suspension of 7.8 g of benzo-1,2,3-thidiazole-7-ethylester-imide hydrochloride in 100 ml of absolute toluene is saturated with hydrogen sulfide under a nitrogen atmosphere at 0° C. for half an hour and a solution of 6.1 g of pyridine in 5 ml of toluene is then added dropwise in the course of three quarters of an hour, while passing in further hydrogen sulfide. When the dropwise addition has ended, hydrogen sulifide is passed in for a further 2 hours and stirring is then continued at room temperature overnight. For working up, the precipitate formed is filtered off and washed thoroughly with toluene and the filtrate is evaporated in vacuo. The residue which remains is purified on flash silica gel (hexane/ethyl acetate). 6.0 g of the title compound of melting point 114°–115° C. result.

1.2 Preparation of S-methyl benzo-1,2,3-thiadiazole-7-thiocarboxylate (compound 1.6)

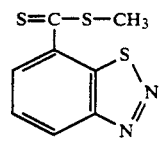

2.10 g of benzo-1,2,3-thiadiazole-7-thiomethyl ester and 2.4 g of Lawesson's reagent are heated at 110° C. in 40 ml of xylene for 28 hours, a further 2.4 g of Lawesson's reagent are then added and the mixture is heated at 130° C. for a further 4 hours. The reaction mixture is then evaporated and the residue is purified on silica gel (flash chromatography, methylene chloride). The title compound is obtained in a yield of 1.9 g having a melting point of 124°–126° C.

1.3 Preparation of benzo-1,2,3-thiadiazole-7-thiocarboxamide (compound 2.1)

A suspension of 2.42 g of p-methoxyphenylthionophosphine sulfide and 1.79 g of benzo-1,2,3-thiadiazole-7-carboxamide in 95 ml of toluene is refluxed under a nitrogen atmosphere for 6 hours. The mixture is then evaporated in vacuo and the residue is suspended in ethyl acetate and filtered off. The filtrate is recrystallized from ethyl acetate/tetrahydrofuran with added active charcoal. 1.1 g of yellow crystals of melting point 129°–131° C. result.

1.4 Preparation of 7-benzo-1,2,3-thiadiazole-N'-N'-dimethylthiohydrazide (compound 3.1)

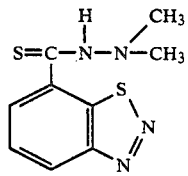

3.2 g of N,N-dimethylhydrazine are added dropwise to 4.52 g of methyl benzo-1,2,3-thiadiazole-7-dithiocarboxylate in 30 ml of tetrahydrofuran at room temperature, while stirring. After a short time, the methyl mercaptan starts to be split off, a beige precipitate separating out. The mixture is heated at 50° C. overnight and on the following day the precipitate is filtered off and washed with methylene chloride. After drying, 2.2 g of the title compound of melting point 195°–197° C. remain.

1.5 Preparation of 7-carboxymethylthio-thiono-benzo-1,2,3-thiadiazole (compound 1.45)

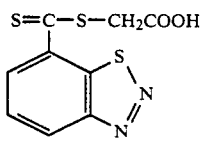

2.9 g of solid 7-chloromethylbenzo-1,2,3-thiadiazole are introduced in portions into a suspension of 1 g of finely triturated sulfur in 8 ml of methanol and 6.4 ml of sodium methylate solution (30% in methanol) at room temperature in the course of 15 minutes, during which the temperature rises to 45° C. The dark suspension is then heated up and stirred at 90° C. for 16 hours. It is then cooled to 0° C., the sodium chloride is filtered off and the filtrate is evaporated. The residue is dissolved in 14 ml of water, 1.9 g of solid sodium chloroacetate are added at 0° C. and stirring is continued at room temperature for 18 hours. For working up, methylene chloride and water are furthermore added to the solution and the organic phase is separated off and extracted again with water. The aqueous extracts are cooled and acidified with concentrated hydrochloric acid at 0° C. The precipitate which has separated out is filtered off, washed with water and recrystallized from ethanol, the title compound of melting point 207°–209° C. resulting.

1.6 Preparation of benzo-1,2,3-thiadiazole-7-ethyl ester-imide hydrochloride (compound 5.2) (intermediate)

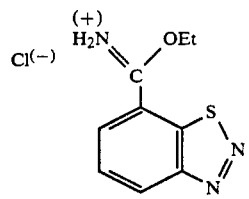

7.2 g of 7-cyanobenzo-1,2,3-thiadiazole are dissolved in 60 ml of absolute ethanol and 20 ml of tetrahydrofuran at 45° C. and the solution is cooled to 0° C. and saturated with gaseous hydrochloric acid at 0° to 15° C. in the course of 1 hour with exclusion of moisture. The reaction mixture is then stored in a refrigerator for 24 hours, 70 ml of absolute diethyl ether are added and the mixture is left to stand in the refrigerator for a further 4 days. The product is then filtered off, washed with diethyl ether and dried. 9.4 g of the compound 5.2 are obtained as beige crystals of melting point 270°–272° C.

1.7 Preparation of 7-hydroxymethyl-benzo-1,2,3-thiadiazole (compound 6.1) (intermediate)

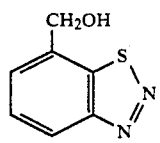

110 ml of triethyl borate are added dropwise to a suspension of 54 g of carboxybenzo-1,2,3-thiadiazole in 420 ml of tetrahydrofuran at room temperature under a nitrogen atmosphere, while stirring, stirring is continued for 1 hour and 45.6 ml of borane-dimethyl sulfide complex in 60 ml of tetrahydrofuran are then added dropwise, with gentle cooling, vigorous evolution of gas being observed. After the mixture has been stirred overnight and left to stand at room temperature, it is cooled again to 5°–10° C. and 200 ml of methanol are added dropwise, while stirring and cooling thoroughly, vigorous evolution of gas again occurring. The mixture is then evaporated in vacuo, a further 300 ml of methanol are added and the mixture is evaporated again. The residue is purified on silica gel (solvent: ethyl acetate/hexane) and the resulting product is recrystallized from ethyl acetate/hexane. The resulting title compound melts at 79°–81° C.

Compounds of the formula V (Table 6) can also be obtained by reducing corresponding esters with excess sodium borohydride in the presence of water in tetrahydrofuran or dioxane at room temperature or at elevated temperature (20°–100° C.).

1.8 Preparation of 6-chloro-7-hydroxymethyl-benzo-1,2,3-thiadiazole (compound 6.1) (intermediate)

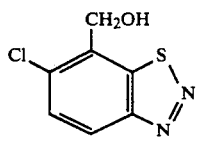

A solution of 1.9 g of 6-chloro-7-carbomethoxybenzo-1,2,3-thiadiazole in 30 ml of tetrahydrofuran (dissolved hot) is added dropwise to a suspension of 4.5 g of sodium borohydride in 30 ml of water and 70 ml of tetrahydrofuran in the course of half an hour, while stirring and heating at 40°–50° C. Heating is continued until the reaction is complete, the mixture is cooled to −20° to −30° C. with a $CO_2$ cooling bath and 15 ml of acetone are added dropwise, vigorous evolution of gas being observed. The reaction mixture is then acidified to pH 3 with 15% hydrochloric acid at −20° C. to −10° C., with further vigorous cooling (evolution of gas), and stirring is continued overnight. The majority of the tetrahydrofuran is then stripped off on a rotary evaporator and the residue is extracted with ethyl acetate. The extracts are washed with water, dried over sodium sulfate and evaporated. The residue gives the title compound of melting point 138°–140° C.

1.9 Preparation of 7-chloromethyl-benzo-1,2,3-thiadiazole (compound 7.1) (Intermediate of the formula VI)

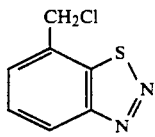

199.2 g of the compound of Example 1.7 are dissolved in 150 ml of methylene chloride and 150 ml of pyridine at 5° C. and initially introduced into the reaction vessel, and a solution of 120 ml of thionyl chloride in 200 ml of methylene chloride is added in the course of three quarters of an hour at 5°–10° C., while cooling. Stirring is then continued overnight at room temperature and the suspension is poured onto ice-water and extracted with methylene chloride. The extracts are washed with ice-water, dried over sodium sulfate, filtered and evaporated. The title compound thus obtained melts at 78°–80° C.

In the compound tables, the associated symbols are used for the following radicals:

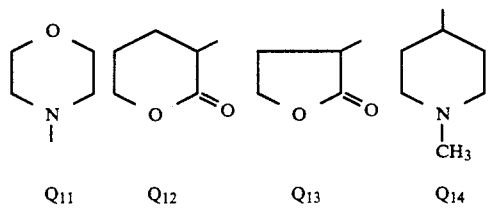

Q11  Q12  Q13  Q14

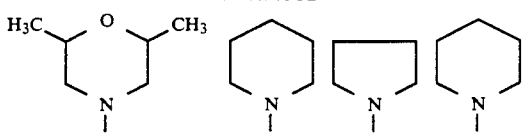

Q15  Q16  Q17  Q18

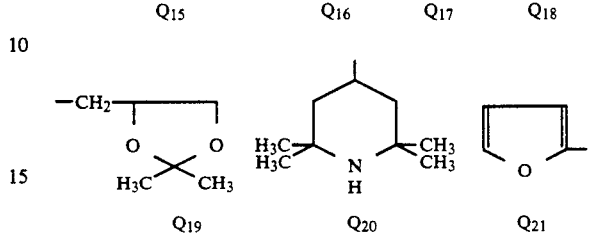

Q19  Q20  Q21

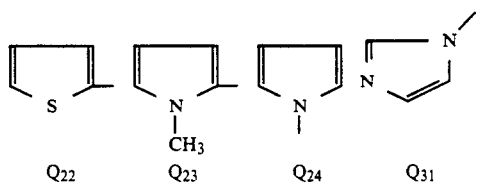

Q22  Q23  Q24  Q31

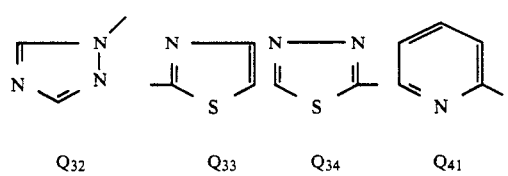

Q32  Q33  Q34  Q41

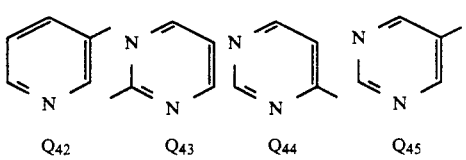

Q42  Q43  Q44  Q45

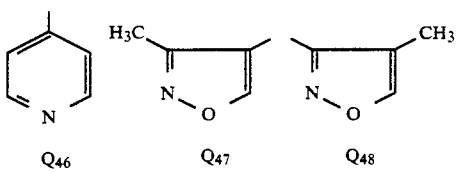

Q46  Q47  Q48

The heterocyclic radicals described above can be substituted by low molecular weight radicals, such as aliphatic radicals having up to 4 C atoms, or by halogen atoms or other radicals.

TABLE 1

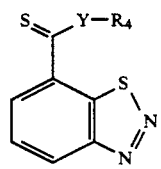

| Compound number | Y | R4 | Physical data |
|---|---|---|---|
| 1.1 | O | Methyl | m.p. 105–108° C. |
| 1.2 | O | Ethyl | m.p. 114–115° C. |
| 1.3 | O | i-Propyl | |
| 1.4 | O | n-Butyl | |

TABLE 1-continued

| Compound number | Y | R4 | Physical data |
|---|---|---|---|
| 1.5 | O | n-Hexyl | |
| 1.6 | S | Methyl | m.p. 124–126° C. |
| 1.7 | S | Ethyl | m.p. 130–132° C. |
| 1.8 | S | n-Propyl | m.p. 92–94° C. |
| 1.9 | S | i-Propyl | |
| 1.10 | S | n-Butyl | |
| 1.11 | S | n-Pentyl | |
| 1.12 | S | t-Butyl | |
| 1.13 | O | Cyclopentyl | |
| 1.14 | O | Cyclohexyl | |
| 1.15 | S | Cyclopentyl | m.p. 117–119° C. |
| 1.16 | S | Cyclohexyl | |
| 1.17 | O | Cyclobutyl | |
| 1.18 | S | Benzyl | |
| 1.19 | O | Benzyl | m.p. 79–81° C. |
| 1.20 | O | H | |
| 1.21 | S | H | |
| 1.22 | O | $CH_2$-Cyclopropyl | m.p. 73–75° C. |
| 1.23 | S | $(CH_2)_2$-Phenyl | |
| 1.24 | S | $CH_2CH_2CH_2$-Phenyl | |
| 1.25 | S | $CH_2CH_2O$-Phenyl | |
| 1.26 | S | 4-Phenoxyphenyl | |
| 1.27 | S | 4-Biphenyl | |
| 1.28 | S | 1-Naphthyl | |
| 1.29 | S | 2-Naphthyl | |
| 1.30 | O | $CH_2CH_2O$-Phenyl | |
| 1.31 | O | 4-Phenoxyphenyl | m.p. 75–78° C. |
| 1.32 | O | 1-Naphthyl | |
| 1.33 | S | Allyl | |
| 1.34 | S | Propargyl | |
| 1.35 | S | 2-Carboxyphenyl | |
| 1.36 | S | n-Octadecyl | |
| 1.37 | O | n-Tricontanyl | |
| 1.38 | S | $CH_2CH_2OCH_3$ | |
| 1.39 | O | $CH_2CH_2SCH_3$ | |
| 1.40 | S | $CH_2$Naphth-1-yl | |
| 1.41 | O | 4-Chlorobenzyl | m.p. 116–118° C. |
| 1.42 | O | $(CH_2)_2-O-(CH_2)_2-O$-Phenyl | |
| 1.43 | S | $(CH_2)_2-O-(CH_2)_2-O-Q_{46}$ | |
| 1.44 | O | Carboxymethyl | |
| 1.45 | S | Carboxymethyl | m.p. 207–209° C. |
| 1.46 | S | 2-Butenyl | |
| 1.47 | S | 4-Hexenyl | |
| 1.48 | S | Phenyl | |
| 1.49 | O | Phenyl | |
| 1.50 | O | 2-Chlorophenyl | |
| 1.51 | S | 4-Chlorophenyl | |
| 1.52 | O | 2-Methoxyphenyl | |
| 1.53 | O | 4-i-Propylphenyl | |
| 1.54 | S | Fluoromethyl | |
| 1.55 | S | $CH_2CH_2-O-Q_{11}$ | |
| 1.56 | O | $Q_{12}$ | |
| 1.57 | S | $Q_{13}$ | |
| 1.58 | S | $Q_{14}$ | |
| 1.59 | O | $CH_2-Q_{21}$ | |
| 1.60 | S | $CH_2-Q_{22}$ | |
| 1.61 | S | $Q_{20}$ | |
| 1.62 | S | $CH_2-Q_{23}$ | |
| 1.63 | S | $Q_{24}$ | |
| 1.64 | S | $Q_{12}$ | |
| 1.65 | S | $CH_2-Q_{31}$ | |
| 1.66 | S | $CH_2-Q_{32}$ | |
| 1.67 | O | $Q_{41}$ | |
| 1.68 | O | $CH_2-Q_{42}$ | |
| 1.69 | O | $CH_2-Q_{45}$ | |
| 1.70 | S | $Q_{44}$ | |
| 1.71 | O | $Q_{46}$ | |
| 1.72 | S | $CH_2-Q_{46}$ | |
| 1.73 | S | Cycloheptyl | |

TABLE 1-continued

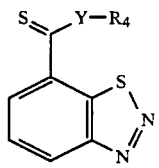

| Compound number | Y | R4 | Physical data |
|---|---|---|---|
| 1.74 | O | $N=C(CH_3)_2$ | |
| 1.75 | O | $N=C(CH_3)$Ethyl | |
| 1.76 | O | $NH_2$ | |
| 1.77 | O | $N(Methyl)_2$ | |
| 1.78 | S | $N(Methyl)_2$ | |
| 1.79 | O | N=cyclohexylidene | |
| 1.80 | O | $N=C(CN)$Phenyl | |
| 1.81 | O | $N=C(CN)CONH_2$ | |
| 1.82 | O | $N=C(CN)CONHCONH$Ethyl | |
| 1.83 | S | $N=C(CN)$Phenyl | |
| 1.84 | S | $N=C(CN)CONH_2$ | |
| 1.85 | S | (benzothiadiazole dithio) | Decomp. from 210° C. |
| 1.86 | O | Cycloheptyl | |
| 1.87 | S | N=cyclopentylidene | |
| 1.88 | S | $Na^\oplus$ | |
| 1.89 | S | $K^\oplus$ | |
| 1.90 | S | $Li^\oplus$ | |
| 1.91 | S | $\frac{1}{2}Ca^{2\oplus}$ | |
| 1.92 | S | $\frac{1}{2}Mg^{2\oplus}$ | |
| 1.93 | S | $HN(Ethyl)_3^\oplus$ | |
| 1.94 | S | $H_2N(i\text{-Propyl})_2^\oplus$ | Resin |
| 1.95 | S | $NH_4^\oplus$ | |
| 1.96 | S | $H\text{-}Q_{16}^\oplus$ | |
| 1.97 | S | $H\text{-}Q_{15}^\oplus$ | |
| 1.98 | S | $\frac{1}{2}(Ba)_2^\oplus$ | |
| 1.99 | O | $Na^\oplus$ | |
| 1.100 | O | $HN(Ethyl)_3^\oplus$ | Resin |

TABLE 1-continued

| Compound number | Y | R4 | Physical data |
|---|---|---|---|
| 1.101 | S | CH2COOMethyl | m.p. 123-125° C. |

TABLE 2

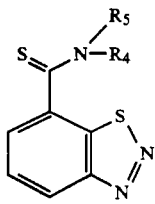

| Compound number | N(R5)R6 | Physical data |
|---|---|---|
| 2.1 | NH2 | m.p. 129-131° C. |
| 2.2 | NH-Methyl | m.p. 210-212° C. |
| 2.3 | N(Methyl)2 | m.p. 118-121° C. |
| 2.4 | NH-Ethyl | |
| 2.5 | NH-Phenyl | |
| 2.6 | NH—CH2—CN | |
| 2.7 | N(CH2CN)2 | |
| 2.8 | NH—CH2COOMethyl | |
| 2.9 | NHCH2C≡CH | |
| 2.10 | NHCH2CH=CH2 | |
| 2.11 | N(CH2CH=CH2)2 | m.p. 82-84° C. |
| 2.12 | NHCH2CH2CN | |
| 2.13 | NH—CH(OEthyl)CN | |
| 2.14 | Q15 | |
| 2.15 | Q16 | m.p. 119-122° C. |
| 2.16 | Q17 | |
| 2.17 | Q18 | |
| 2.18 | NH-Q12 | |
| 2.19 | Q31 | |
| 2.20 | Q32 | |
| 2.21 | NH-Q33 | |
| 2.22 | NH-Q34 | |
| 2.23 | NH-Q41 | |
| 2.24 | NH-Q42 | |
| 2.25 | NH-Q43 | |
| 2.26 | NH-Q44 | |
| 2.27 | N(CH3)-Q45 | |
| 2.28 | NH-Q46 | |
| 2.29 | NH-Q47 | |
| 2.30 | NH-Q48 | |
| 2.31 | NH-Q12 | |
| 2.32 | NHCH2-Q21 | m.p. 174-176° C. |
| 2.33 | NHCH2-Phenyl | |
| 2.34 | N(CH2Phenyl)2 | |
| 2.35 | NH(3,5-Dichlorophenyl) | |
| 2.36 | NH(2-Methylphenyl) | |
| 2.37 | NHOH | Decomp. 133°C. |
| 2.38 | N(Methyl)-O-Methyl | |
| 2.39 | NH—O-Cyclohexyl | |
| 2.40 | NH—O-n-Octyl | |
| 2.41 | N(O-Alkyl)-O-Allyl | |
| 2.42 | NH—O-Phenyl | |
| 2.43 | Q11 | m.p. 178-180° C. |

TABLE 3

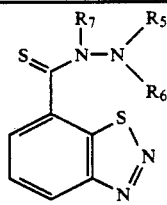

| Compound number | R7 | R5 | R6 | Physical data |
|---|---|---|---|---|
| 3.1 | H | Methyl | Methyl | m.p. 195-197° C. |
| 3.2 | H | H | H | |
| 3.3 | H | Methyl | H | |
| 3.4 | Methyl | Methyl | Methyl | |
| 3.5 | Ethyl | Phenyl | H | |
| 3.6* | H | Phenyl | H | m.p. 110-111° C. |
| 3.7 | H | Benzyl | Benzyl | |
| 3.8 | H | Methyl | Phenyl | |
| 3.9 | H | Phenyl | Phenyl | |
| 3.10 | H | 1-Naphthyl | H | |
| 3.11 | H | H | Benzyl | |
| 3.12 | H | —CH2CH2CH2CH2— | | |
| 3.13 | H | —CH2CH2CH2CH2CH2— | | m.p. 166-168° C. |
| 3.14 | Me | —CH2CH2CH2CH2CH2CH2— | | |
| 3.15 | H | 2-Fluorophenyl | H | |
| 3.16 | H | 4-Methylphenyl | H | |
| 3.17 | H | 4-Chlorobenzyl | H | |
| 3.18 | H | Q41 | H | |
| 3.19 | H | Q43 | H | |
| 3.20 | Ethyl | Q41 | Ethyl | |
| 3.21 | H | Q33 | H | |
| 3.22 | H | 2-Naphthyl | H | |

*In the form of the tetrabutylammonium salt

TABLE 4

| Compound number | R1, R2, R3 | A | Physical data |
|---|---|---|---|
| 4.1 | 4-Fluoro | NH—NH2 | |
| 4.2 | 5-Fluoro | NH—N(Methyl)2 | |
| 4.3 | 5-Fluoro | N(Methyl)-N(Methyl)2 | |
| 4.4 | 5-Fluoro | S-n-Propyl | |
| 4.5 | 5-Fluoro | S-Methyl | m.p. 122-124° C. |
| 4.6 | 5-Fluoro | S-Benzyl | |
| 4.7 | 5-Fluoro | S-Phenyl | |
| 4.8 | 5-Fluoro | S—CH2-Q21 | |
| 4.9 | 5-Fluoro | S-Cyclopentyl | |
| 4.10 | 5-Fluoro | S-Cyclohexyl | |
| 4.11 | 5-Fluoro | SK | |
| 4.12 | 5-Fluoro | SH | |
| 4.13 | 5-Fluoro | SH.NH3 | |
| 4.14 | 5-Fluoro | NHOH | |
| 4.15 | 5-Fluoro | N(Methyl)O-Methyl | |

TABLE 4-continued

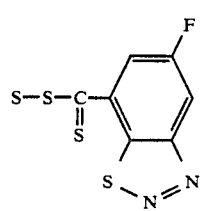

| Compound number | R₁, R₂, R₃ | A | Physical data |
|---|---|---|---|
| 4.16 | 5-Fluoro | 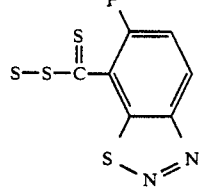 | |
| 4.17 | 5-Fluoro | O-Methyl | m.p. 104–107° C. |
| 4.18 | 5-Fluoro | O-i-Propyl | |
| 4.19 | 5-Fluoro | O-Benzyl | |
| 4.20 | 5-Fluoro | OH | |
| 4.21 | 5-Fluoro | O—N=C(CN)CONH₂ | |
| 4.22 | 5-Fluoro | S-Q₁₃ | |
| 4.23 | 6-Fluoro | O-Methyl | |
| 4.24 | 6-Fluoro | S-Methyl | |
| 4.25 | 6-Fluoro | S-Ethyl | |
| 4.26 | 6-Fluoro | S-Phenyl | |
| 4.27 | 6-Fluoro | NH₂ | |
| 4.28 | 6-Fluoro | NH-Methyl | |
| 4.29 | 6-Fluoro | NH-Propyl | |
| 4.30 | 6-Fluoro | NH—CH₂-Q₂₁ | |
| 4.31 | 6-Fluoro | N(Methyl)-O-methyl | |
| 4.32 | 6-Fluoro | S-n-Propyl | |
| 4.33 | 6-Fluoro | S-Benzyl | |
| 4.34 | 6-Fluoro | O-Benzyl | |
| 4.35 | 6-Fluoro | O-4-Methoxybenzyl | |
| 4.36 | 6-Fluoro | S-4-Phenoxyphenyl | |
| 4.37 | 6-Fluoro | SH | |
| 4.38 | 6-Fluoro | SNa | |
| 4.39 | 6-Fluoro | SH.N(Ethyl)₃ | |
| 4.40 | 6-Fluoro | 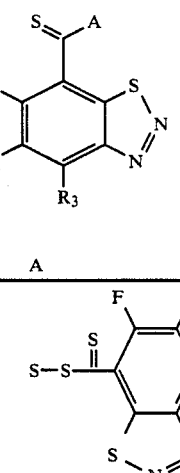 | |
| 4.41 | 6-Fluoro | NH—NH₂ | |
| 4.42 | 6-Fluoro | NH—N(Methyl)₂ | |
| 4.43 | 5-Fluoro | NH₂ | |
| 4.44 | 5-Fluoro | Q₁₆ | |
| 4.45 | 5-Fluoro | NH-Q₄₅ | |
| 4.46 | 5-Fluoro | NH-Q₄₃ | |
| 4.47 | 5-Fluoro | NH-Q₄₈ | |
| 4.48 | 5-Fluoro | NH-Q₃₃ | |
| 4.49 | 5-Fluoro | NH—OH | |
| 4.50 | 4-Fluoro | O-Methyl | |
| 4.51 | 4-Fluoro | S-Methyl | |
| 4.52 | 4,6-Difluoro | O-Ethyl | |
| 4.53 | 4,6-Difluoro | O-Benzyl | |
| 4.54 | 4,6-Difluoro | S-Phenyl | |
| 4.55 | 4,6-Difluoro | OH | |
| 4.56 | 4,6-Difluoro | NH₂ | |
| 4.57 | 4,6-Difluoro | OLi | |
| 4.58 | 4,5,6-Trifluoro | O-Methyl | |
| 4.59 | 4,5,6-Trifluoro | S-Methyl | |
| 4.60 | 4,5,6-Trifluoro | OH | |
| 4.61 | 4,5,6-Trifluoro | 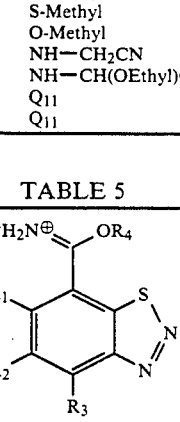 | |
| 4.62 | 6-Chloro | O-Methyl | |
| 4.63 | 5-Chloro | S-Methyl | |
| 4.64 | 4-Bromo | O-Methyl | |
| 4.65 | 6-Fluoro | NH—CH₂CN | |
| 4.66 | 6-Fluoro | NH—CH(OEthyl)CN | |
| 4.67 | 5-Fluoro | Q₁₁ | |
| 4.68 | 6-Fluoro | Q₁₁ | |

TABLE 5

| Compound number | R₁, R₂, R₃ | R₄ | Physical data |
|---|---|---|---|
| 5.1 | H | Methyl | |
| 5.2 | H | Ethyl | m.p. 270–272° C. |
| 5.3 | H | n-Propyl | |
| 5.4 | H | i-Propyl | |
| 5.5 | 5-F | n-Butyl | |
| 5.6 | 4,6-Di-F | sec.-Butyl | |
| 5.7 | 6-F | n-Octyl | |
| 5.8 | H | n-Dodceyl | |
| 5.9 | H | Cyclopentyl | |
| 5.10 | 6-F | Cyclohexyl | |
| 5.11 | 5-F | Methyl | |
| 5.12 | 5-F | Ethyl | |
| 5.13 | 6-F | Ethyl | |
| 5.14 | 4,5,6-Tri-F | n-Propyl | |
| 5.15 | 5-Br | n-Butyl | |
| 5.16 | 6-Cl | Methyl | |
| 5.17 | 4-F | Methyl | |

TABLE 6

| Compound number | R₁, R₂, R₃ | Physical data |
|---|---|---|
| 6.1 | H | m.p. 79–81° C. |

TABLE 6-continued $$\text{structure: benzothiadiazole with } CH_2OH \text{ at position 7, } R_1 \text{ at 6, } R_2 \text{ at 5, } R_3 \text{ at 4}$$

| Compound number | $R_1, R_2, R_3$ | Physical data |
|---|---|---|
| 6.2 | 5-F | |
| 6.3 | 5-Cl | |
| 6.4 | 5-Br | |
| 6.5 | 6-F | |
| 6.6 | 6-Cl | m.p. 138–140° C. |
| 6.7 | 6-Br | |
| 6.8 | 6-I | |
| 6.9 | 5-I | |
| 6.10 | 4-F | |
| 6.11 | 5,6-Di-F | |
| 6.12 | 4,5-Di-F | |
| 6.13 | 4,6-Di-Cl | |
| 6.14 | 6-Methoxy | |
| 6.15 | 5-Methylthio | |
| 6.16 | 6-Methylthio | |
| 6.17 | 4-Methoxy | |
| 6.18 | 4-Methyl | |

TABLE 7

$$\text{structure: benzothiadiazole with } CH_2Hal \text{ at position 7, } R_1 \text{ at 6, } R_2 \text{ at 5, } R_3 \text{ at 4}$$

| Compound number | $R_1, R_2, R_3$ | Hal | Physical data |
|---|---|---|---|
| 7.1 | H | Cl | m.p. 78–80° C. |
| 7.2 | H | Br | |
| 7.3 | H | I | |
| 7.4 | 6-F | Cl | |
| 7.5 | 6-Cl | Cl | |
| 7.6 | 6-Br | Br | |
| 7.7 | 6-I | Cl | |
| 7.8 | 5-F | Cl | |
| 7.9 | 4,5-Di-F | Cl | |
| 7.10 | 5-F | Br | |
| 7.11 | 4-F | Cl | |
| 7.12 | 4,6-Di-Cl | Cl | |
| 7.13 | 5,6-Di-F | Cl | |

Formulation examples for active sustances from the tables (% = percent by weight

| 2.1 Wettable powder | a) | b) | c) |
|---|---|---|---|
| Active substance from the tables | 25% | 50% | 75% |
| Na lignin-sulfonate | 5% | 5% | — |
| Na lauryl sulfate | 3% | — | 5% |
| Na diisobutylnaphthalene sulfonate | — | 6% | 10% |
| Octylphenolpolyethylene glycol ether (7–8 mol of ethylene oxide) | — | 2% | — |
| Highly disperse silicic acid | 5% | 10% | 10% |
| Kaolin | 62% | 27% | — |

The active substance is mixed with the additives and the mixture is ground homogeneously in a suitable mill. Wettable powders which can be diluted with water to give suspensions of any desired concentration are obtained.

| 2.2 Emulsion concentrate | |
|---|---|
| Active substance from the tables | 10% |
| Octylphenolpolyethylene glycol ether (4–5 mol of ethylene oxide) | 3% |
| Ca dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| 2.3 Dust | a) | b) |
|---|---|---|
| Active substance from the tables | 5% | 8% |
| Talc | 95% | — |
| Kaolin | — | 92% |

Ready-to-use dusts are obtained by mixing the active substance with the carriers and grinding the mixture on a suitable mill.

| 2.4 Extruded granules | |
|---|---|
| Active substance from the tables | 10% |
| Na lignin-sulfonate | 2% |
| Carboxymethylcellulose | 1% |
| Kaolin | 87% |

The active substance is mixed with the additives and the mixture is ground and moistened with water. This mixture is extruded and then dried in a stream of air.

| 2.5 Coated granules | |
|---|---|
| Active substance from the tables | 3% |
| Polyethylene glycol (MW 200) | 3% |
| Kaolin | 94% |
| (MW = molecular weight) | |

The finely ground active substance is applied uniformly to the kaolin, moistened with polyethylene glycol in a mixer. Dust-free coated granules are obtained in this way.

| 2.6 Suspension concentrate | |
|---|---|
| Active substance from the tables | 40% |
| Ethylene glycol | 10% |
| Nonylphenolpolyethylene glycol ether (15 mol of ethylene oxide) | 6% |
| Na lignin-sulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is intimately mixed with the additives. A suspension concentrate is obtained, from which suspensions of any desired concentration can be prepared by dilution with water.

3. BIOLOGICAL EXAMPLES

Example 3.1: Action against *Colletotrichum lagenarium* on *Cucumis sativus* L.

a) After growing for 2 weeks, cucumber plants are sprayed with a spray liquor prepared from a wettable powder of the active substance (concentration: 200 ppm). After 48 hours, the plants are infected with a spore suspension ($1.5 \times 10^5$ spores/ml) of the fungus and incubated at a high atmospheric humidity and a temperature of 23° C. for 36 hours. The incubation is then continued at normal atmospheric humidity and at 22° C. to 23° C.

The protective action is evaluated on the basis of the fungal attack 7–8 days after infection.

b) After growing for 2 weeks, cucumber plants are treated by soil application with a spray liquor prepared from a wettable powder of the active substance (concentration: 60 or 20 ppm, based on the soil volume). After 48 hours, the plants are infected with a spore suspension ($1.5 \times 10^5$ spores/ml) of the fungus and incubated at a high atmospheric humidity and a temperature of 23° C. for 36 hours. The incubation is then continued at normal atmospheric humidity and at 22° C.

The protective action is evaluated on the basis of the fungal attack 7–8 days after infection.

c) After growing for 2 weeks, cucumber plants are sprayed with a spray liquor prepared from a wettable powder of the active substance (concentration: 200 ppm).

After 3 weeks, the plants are infected with a spore suspension ($1.5 \times 10^5$ spores/ml) of the fungus and incubated at a high atmospheric humidity and a temperature of 23° C. for 36 hours. The incubation is then continued at normal atmospheric humidity and at 22° to 23° C.

The protective action is evaluated on the basis of the fungal attack 7–8 days after infection.

In tests (a) and (b), compounds from Tables 1 to 7 show a good action. Thus, for example, compounds 1.1, 1.6, 1.7, 1.8, 1.15, 1.101, 2.1, 2.11, 2.16, 3.6, 5.2, 6.1 and 7.1 reduce the fungal attack to 0 to 20%. In contrast, control plants which were untreated but infected show a Colletotrichum attack of 100%.

Example 3.2: Action against *Puccinia graminis* on Wheat a) 6 days after sowing, wheat plants are sprayed with a spray liquor prepared from a wettable powder of the active substance (0.02% of active substance). After 24 hours, the treated plants are infected with a uredo spore suspension of the fungus. After incubation at 95–100% relative atmospheric humidity and about 20° C. for 48 hours, the infected plants are placed in a greenhouse at about 22° C. The rust pustule development is evaluated 12 days after infection.

b) 5 days after sowing, wheat plants are watered with a spray liquor prepared from a wettable powder of the active substance (0.006% of active substance, based on the soil volume). After 48 hours, the treated plants are infected with a uredo spore suspension of the fungus. After incubation at 95–100% relative atmospheric humidity and about 20° C. for 48 hours, the infected plants are placed in a greenhouse at about 22° C. The rust pustule development is evaluated 12 days after infection.

Compounds from Tables 1 to 7 show a good action against Puccinia fungi. Thus, for example, compounds 1.1, 1.2, 1.6, 1.8, 1.101, 2.11, 2.16 and 5.2 reduce the fungal attack to 0 to 20%. In contrast, control plants which were untreated but infected show a PucciniA attack of 100%.

Example 3.3: Action against *Phytophthora infestans* on Tomato Plants a) After growing for 3 weeks, tomato plants are sprayed with a spray liquor prepared from a wettable powder of the active substance (0.02% of active substance). After 24 hours, the treated plants are infected with a sporangia suspension of the fungus. The fungal attack was evaluated after incubation of the infected plants at 90–100% relative atmospheric humidity and 20° C. for 5 days.

b) After growing for 3 weeks, tomato plants are watered with a spray liquor prepared from a wettable powder of the active substance (0.006% of active substance based on the soil volume). It is ensured that the spray liquor does not come into contact with the aboveground parts of the plants. After 48 hours, the treated plants are infected with a sporangia suspension of the fungus. The fungal attack is evaluated after incubation of the infected plants at 90–100% relative atmospheric humidity and 20° C. for 5 days.

Compounds from Tables 1 to 7 show a good protective action against the Phytophthora fungus. Thus, for example, compounds 1.1, 1.2, 1.101, 2.1, 2.11, 2.16, 5.2 and 6.1 reduced the fungal attack to 0 to 20%. In contrast, control plants which were untreated but infected show a Phytophthora attack of 100%.

Example 3.4: Action against *Pyricularia oryzae* on Rice Plants a) After growing for 2 weeks, rice plants are sprayed with a spray liquor prepared from a wettable powder of the active substance (0.02% of active substance). After 48 hours, the treated plants are infected with a conidia suspension of the fungus. After incubation at 95–100% relative atmospheric humidity and 24° C. for 5 days, the fungal attack is evaluated.

b) Rice plants 2 weeks old are watered with a spray liquor prepared from a wettable powder of the active substance (0.006% of active substance, based on the soil volume). The pots are then filled with water so that the lowest parts of the stems of the rice plants are standing in water. After 96 hours, the treated rice plants are infected with a conidia suspension of the fungus. After incubation of the infected plants at 95–100% relative atmospheric humidity and about 24° C. for 5 days, the fungal attack is evaluated.

Rice plants which are treated with a spray liquor containing a compound from Tables 1 to 7 as the active substance show only mild fungal attack in comparison with untreated control plants (100% attack). Thus, for example, compounds 1.1, 1.2, 1.7, 1.8, 2.1, 2.16, 5.2, 6.1 and 7.1 reduce the attack to 0 to 20% in test (a), and compounds 1.1, 1.6, 1.7, 2.11, 2.16, 3.1 and 6.1 reduce the attack to 0 to 20% in test (b).

Example 3.5: Action against *Peronospora tabacina* on Tobacco Plants

A) Leaf application

Tobacco plants (8 weeks old) are sprayed with a formulated solution of the active substance (concentration: 0.02% of active substance). Four days after the treatment, the plants are innoculated with a sporangia suspension of *Peronospora tabacina* ($10^4$ sproangia/ml), kept in the dark at 25° C. and a high atmospheric humidity for 20 hours and then incubated further in a normal day/night alternating sequence.

B) Soil application

Tobacco plants (8 weeks old) are treated by soil application with a formulated solution of the active substance (concentration: 0.006% of active substance, based on the soil volume). After 4 days, the plants are innoculated with a sporangia suspension of *Peronospora tabacina* ($10^4$ sporangia/ml), kept in the dark at 25° C. and a high atmospheric humidity for 20 hours and then incubated further under a normal day/night alternating sequence.

The symptoms in tests A and B are evaluated on the basis of the leaf surface attacked by fungus.

The control plants show an attack of 90 to 100%. Plants which had been treated with compound 2.1 in test A showed an attack of 0-30%.

Example 3.6: Action against *Bremia letucae* on Lettuce

Lettuce plants two weeks old are watered with a formulated solution of the active substance (0.002% of active substance, based on the soil volume). After 5 days, the treated plants are innoculated with a spore suspension of the fungus ($5 \times 10^4$ spores/ml). The plants are incubated at 18° C. first under a hood (relative atmospheric humidity of 90-100%) for 2 days and then without a hood for 7 days. To bring the fungus to sporulation, the plants are placed under a hood again for 3 days.

The fungal attack is evaluated 12 days after the innoculation on the basis of the leaf surface attacked by fungus.

Compounds from Tables 1-7 show a good action against Bremia. Thus, plants which were treated with, for example, compound 2.1 remained largely free from attack (0-30% damage). In contrast, plants which were untreated but infected (control) showed a Bremia attack of 100%.

Example 3.7: Action against *Erysiphe graminis* on Wheat

After growing for 5 days, wheat plants are sprayed with a spray liquor prepared from a wettable powder of the active substance (concentration: 0.02%). One day later, the plants are infected with conidia of *Erysiphe graminis* and incubated at 20° C.

The protective action is evaluated on the basis of the fungal attack 8-10 days after infection.

In this test, compounds from Table 1 to 7 employed as the active substance show a good action against *Erysiphe graminis*. Thus, plants which were treated with, for example, compound 1.6 or 2.1 remained largely free from Erysiphe attack (0 to 30% damage). In contrast, plants which were untreated but infected (control) show a Erysiphe attack of 100%.

What is claimed is:

1. A compound of the formula V

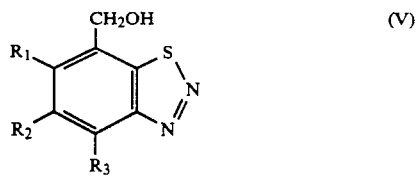

in which: $R_1$, $R_2$ and $R_3$ independently of one another are hydrogen, halogen, methyl, methoxy or methylthio.

2. A compound of the formula VI

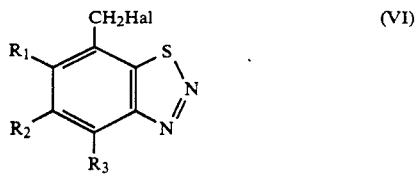

in which: $R_1$, $R_2$ and $R_3$ independently of one another are hydrogen, halogen, methyl, methoxy or methylthio and Hal is halogen.

* * * * *